United States Patent [19]

Lowne et al.

[11] Patent Number: 5,357,343
[45] Date of Patent: Oct. 18, 1994

[54] SPECTROPHOTOMETER HAVING MEANS FOR SIMULTANEOUS MODULATION, SWITCHING AND WAVELENGTH SELECTION OF A LIGHT SOURCE

[75] Inventors: Alan J. Lowne, victor; James R. Sandifer, Rochester; David S. Uerz, Ontario; Steven C. Switalski; Hsue-Yang Liu, both of Rochester, all of N.Y.

[73] Assignee: Eastman Kodak Company, Rochester, N.Y.

[21] Appl. No.: 951,607

[22] Filed: Sep. 28, 1992

Related U.S. Application Data

[63] Continuation of Ser. No. 737,824, Jul. 26, 1991, abandoned, which is a continuation-in-part of Ser. No. 591,204, Oct. 1, 1990, abandoned.

[51] Int. Cl.$^5$ .......................... G01N 21/25; G01J 3/00
[52] U.S. Cl. .................... 356/418; 356/419; 356/51; 250/351
[58] Field of Search ............ 356/319, 320–321, 356/323–326, 414–420, 51; 250/351, 339

[56] References Cited

U.S. PATENT DOCUMENTS

| | | | |
|---|---|---|---|
| 3,780,299 | 12/1973 | Bock . | |
| 3,999,062 | 12/1976 | Demsky et al. | 250/227 |
| 4,061,428 | 12/1977 | Amano et al. | 250/226 X |
| 4,097,743 | 6/1978 | Carlson | 250/339 |
| 4,291,985 | 9/1981 | Tsujimura | 356/408 |
| 4,305,663 | 12/1981 | Perkins et al. | 356/323 |
| 4,477,190 | 10/1984 | Listen et al. | 356/418 |
| 4,644,485 | 2/1987 | Ferber et al. | 356/323 |
| 4,648,714 | 3/1987 | Benner et al. | 356/301 |
| 4,945,250 | 7/1990 | Bowen et al. | 250/461.1 |
| 4,977,325 | 12/1990 | Bowen et al. | 250/461.2 |

FOREIGN PATENT DOCUMENTS

291855A5 7/1991 Fed. Rep. of Germany .

OTHER PUBLICATIONS

Konnerth et al., "In–Situ Measurement", IEEE Transactions (Jul. 1975), pp. 452–456.
D. L. Wetzel, "Near–infrared Reflectance Analysis", Anal. Chem., 55(1983)1165A–1166A.
S. C. Stinson, "Advances Made in Applying IR Sensors to Process Control", Chem. and Eng. News, Jan., 1989, pp. 30–31.
P. Dubois, et al., "Determination of Five Components in a Pharmaceutical Formulation Using Near Infrared Relectance Spectrophotometers", Analyst, vol., 112, p. 1675 (1987).
B. R. Buchanan et al., "Detection of Ethanol in wines Using Optical–Fiber Measurements and Near–Infrared Analysis", Appl. Spect., vol., 42, p. 1106, (1988).
Instruction Manual, Microquad 8000, Nov. 25, 1984, pp. 1.1–2.6.
"Iota A New Computer Controlled Thin Film Thickness Measurement Tool", 1972, vol. 15, pp. 371–380, Konnerth et al.
Introduction to Solid–State Television Systems, "Color and Black & white", pp. 128–131 date unknown.
Detection of Signals in Noise, 1971, pp. 239–241.
Optical Coating Laboratory, Inc., Stock Filter Catalog 1990–1991 pp. 4, 28–36.

*Primary Examiner*—Vincent P. McGraw
*Assistant Examiner*—K. P. Hantis
*Attorney, Agent, or Firm*—Clyde E. Bailey

[57] ABSTRACT

A spectrophotometer is described, comprising a single light source, a single detector, optics for dually and alternatively reading a sample and a reference, and only one moving part. That moving part is a chopper containing multiple pass-through apertures, each filled with a unique bandpass filter to select wavelengths to specifically illuminate the sample or reference. To inform the spectrophotometer whether and when it is reading the sample or the reference, trigger means are provided in at least twice the number of the pass-through apertures.

11 Claims, 8 Drawing Sheets

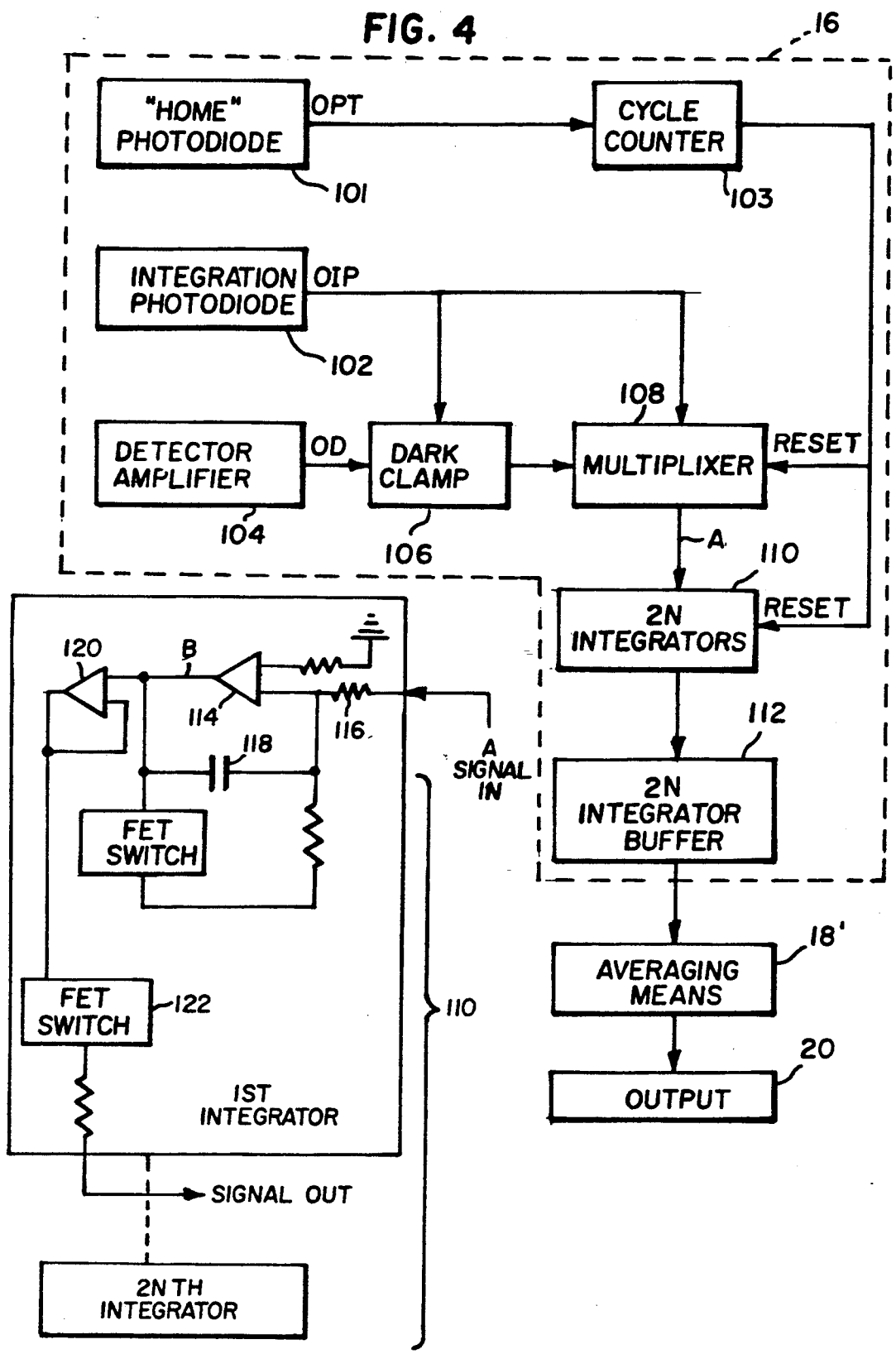

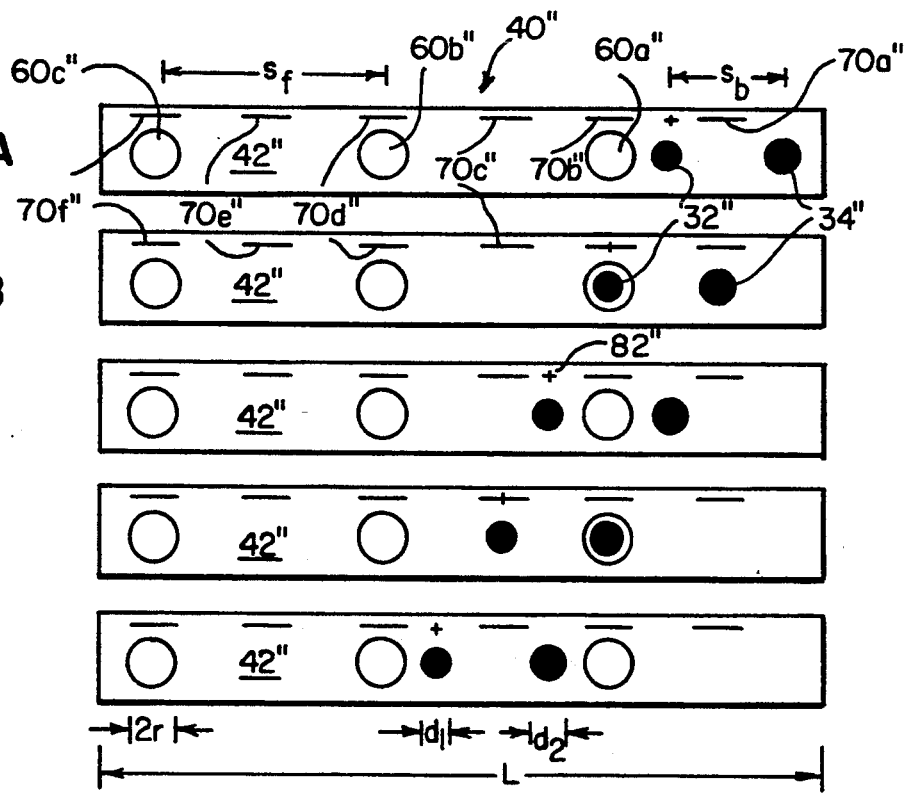
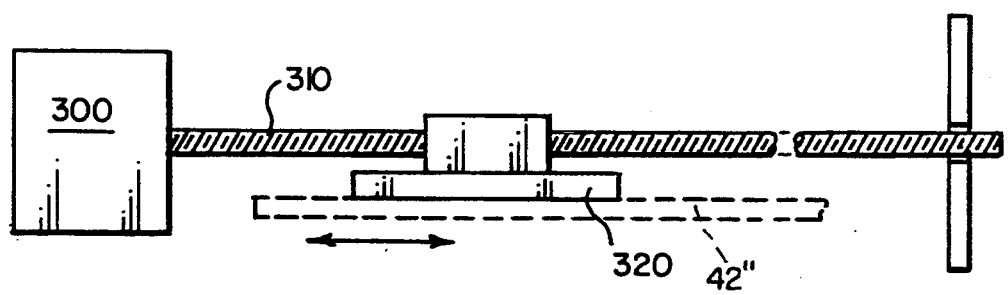
FIG. 9

SPECTROPHOTOMETER HAVING MEANS FOR SIMULTANEOUS MODULATION, SWITCHING AND WAVELENGTH SELECTION OF A LIGHT SOURCE

This is a continuation of application Ser. No. 737,824, filed Jul. 26, 1991, now abandoned, which is a continuation-in-part of application Ser. No. 591,204 filed Oct. 1, 1980, now abandoned.

FIELD OF THE INVENTION

The present invention relates to spectroscopy—especially, but not confined to, near infrared spectroscopy. There are many applications for spectrophotometers which operate within this wavelength range. These include agricultural applications such as the analysis of water and protein in grain, various medical applications, industrial applications such as process control and various applications in the pharmaceutical and biotechnology industries.

BACKGROUND OF THE INVENTION

The noted applications require simple, cheap and rubbed spectrophotometers which are easy to maintain, can be purchased in large quantities and can be used in harsh environments. In addition, accuracy requirements such as photometric stability, wavelength resolution, and spectral reproducibility must be equal to or better than that possessed by state-of-the-art instruments. The objective of the present invention is to achieve the above requirements.

Photometer devices are known in the prior art that use a single light source, a single detector and a dual beam fiber optics that splits the light into a reference beam and a sample beam. Such devices are shown, for example, in U.S. Pat. No. 4,061,428 and an article by Konnerth et al entitled "In-Situ Measurement", IEEE Transactions (7/75). A common feature of such prior devices is the use of a chopper wheel having apertured portions to allow both the reference beam and the sample beam to pass through a selected filter in the aperture. However, considering the device of the '428 patent, it is noteworthy that the triggering apertures 33 in chopper wheel 22 are identical in number to the filter apertures 24. That is, there are disclosed 3N apertures 24 and 3N apertures 33. Further, the angular placement of apertures 24 is the same as such placement of the bifurcated fiber optics 17 and 14. As a result, the only way to prevent both the sample beam and the reference beam to arrive at the detector simultaneously (an unacceptable result), is to position an oscillating shutter 46 adjacent to chopper 22. (Although there are N more apertures 38 also in chopper 22, these are used to detect red versus green versus blue filters, and do not control whether a reference beam or a sample beam is in place). Such a use of a chopper and a shutter has a decided disadvantage—there are at least two moving parts required. Moving parts are well-known to be the cause of mechanical breakdown.

Hence, prior to this invention, the problem has been that a spectrophotometer has not been provided with a single light source, a single detector, split optics for dually detecting both a sample and a reference using the single source and single detector, and means for triggering and collecting either the sample beam or the reference beam for detection, wherein only one moving part is present in the optics.

In the Konnerth article noted above, there appears to be only one moving part in the spectrophotometer of FIG. 1. However, the article does not describe the use of a triggering mechanism whereby the motor and chopper inform the computer where the chopper is. Instead, the computer drives the motor. This is insufficient because the accuracy and timing of the positioning has to be exact. For such an arrangement, the costs are high. A more preferred system is one in which the positioning can have wide tolerances because the actual rather than theoretical positioning is detected.

More recent attempts to provide spectrophotometers have not solved the noted problems. U.S. Pat. No. 4,648,714 teaches a dual beam spectrophotometer having a single moving part (chopper 58 with four filter apertures 17(a)–17(d)). However, it does this at the expense of two detectors (19 and 37). The use of two different detectors is well known to be a source of drift error.

SUMMARY OF THE INVENTION

We have constructed a spectrophotometer that solves the aforementioned problems.

More specifically, in accord with one aspect of the invention, there is provided a spectrophotometer comprising a single light source, a single detector, signal generating means responsive to the detector for generating a signal representing the amount of light detected by the detector, optic means for separately illuminating both a reference and a sample with a light beam from the source that is transmitted to the detector, the optic means including a rotatable chopper and means for rotating the chopper to intercept the light beam, the optic means being constructed to alternately pass through the chopper a light beam for the reference and a light beam for the sample, the chopper further including a) a plurality of pass-through apertures, each with a bandpass filter constructed to pass through the chopper only light of preselected wavelengths, the optic means being further constructed and positioned to direct the reference light beam and the sample light beam at illumination spots on the chopper that are aligned with the circle of rotation of the pass-through apertures, and b) a plurality of trigger means for sensing when the pass-through filters are aligned with one of the light beams, the trigger means being separately operatively connected to the signal-generating means. The spectrophotometer is improved in that the illumination spots on the chopper are disposed at an angle that is smaller than the degrees of the angular separation of the pass-through apertures, and in that the trigger means are at least double in number the pass-through apertures, so that the trigger means alternately control the detection of light: from the reference beam and the sample beam that is illuminating a given pass-through aperture.

In accord with another aspect of the invention, there is provided such a spectrophotometer as noted in the first sentence of the previous paragraph, improved in that the maximum number N of the pass-through apertures is defined by the following formula:

(1) $N < 2\Pi R/(d_1 + d_2 + 4r)$ wherein R=the radius of the centers of the pass-through apertures, r=the radius of the pass-through apertures, and $d_1$ and $d_2$=the diameter of the light beams for the reference and sample, respectively, so that the pass-through apertures are spaced apart a distance sufficient to ensure that, between each transmittal of one of the beams through the chopper, there is a time when no light beam is transmitted.

Accordingly, it is an advantageous feature of the invention that an inexpensive, yet reliable spectrophotometer is provided, the reliability residing in the use of a single light source, single detector, split optics to detect a reference and yet only one moving part.

Other advantageous features will become apparent upon reference to the following Description of the Preferred Embodiments, when read in light of the attached drawings.

BRIEF DESCRIPTION OF THE DRAWINGS

FIG. 4 is a schematic diagram of the associated electronics used with the remainder of the spectrophotometer illustrated in FIG. 1;

FIG. 6 is an expanded circuit diagram of the integrator portion of the diagram of FIG. 5.

FIG. 8A–8E are schematic illustrations of the invention using a linear chopper that is reciprocated; and FIG. 9 is a fragmentary schematic view of the drive for the linear chopper.

DESCRIPTION OF THE PREFERRED EMBODIMENTS

The invention is hereinafter described by reference to a preferred embodiment, which features bifurcated fiber optics in a spectrophotometer designed to analyze the chemical components of a chemical synthesis plant. In addition, the invention is useful regardless whether fiber optics are used to split the light beam or not, and regardless of the end use of the instrument. Thus, the test sample being analyzed can also be an analyte of a body liquid, such as glucose or cholesterol, or the spectrophotometer can be employed for other purposes. Useful examples include those described in:

D. L. Wetzel, "Near-infrared Reflectance Analysis", Anal. Chem., 55(1983)1165A;

S. C. Stinson, "Advances Made in Applying IR Sensors to Process Control", Chem. and Eng. News, January, 1989, p. 30;

P. Dubois, et al, "Determination of Five Components in a Pharmaceutical Formulation Using Near Infrared Reflectance Spectrophotometers", Analyst, Vol. 112, p. 1675 (1987); and B. R. Buchanan et al, "Detection of Ethanol in Wines Using Optical-Fiber Measurements and Near-Infrared Analysis", Appl. Spect., Vol. 42, p. 1106 (1988).

Although designed to operate principally in the near infrared region of the spectrum, the instrument can be readily modified by changing source and detector to operate over a much broader wavelength range, extending from below 400 nm to over 2800 nm, by employing well known principles of detecting visible and infrared radiation as shown by W. L. Wolfe, G. J. Zissis, eds., "The Infrared Handbook", Environmental Research Institute of Michigan, 1978.

Figure 1:
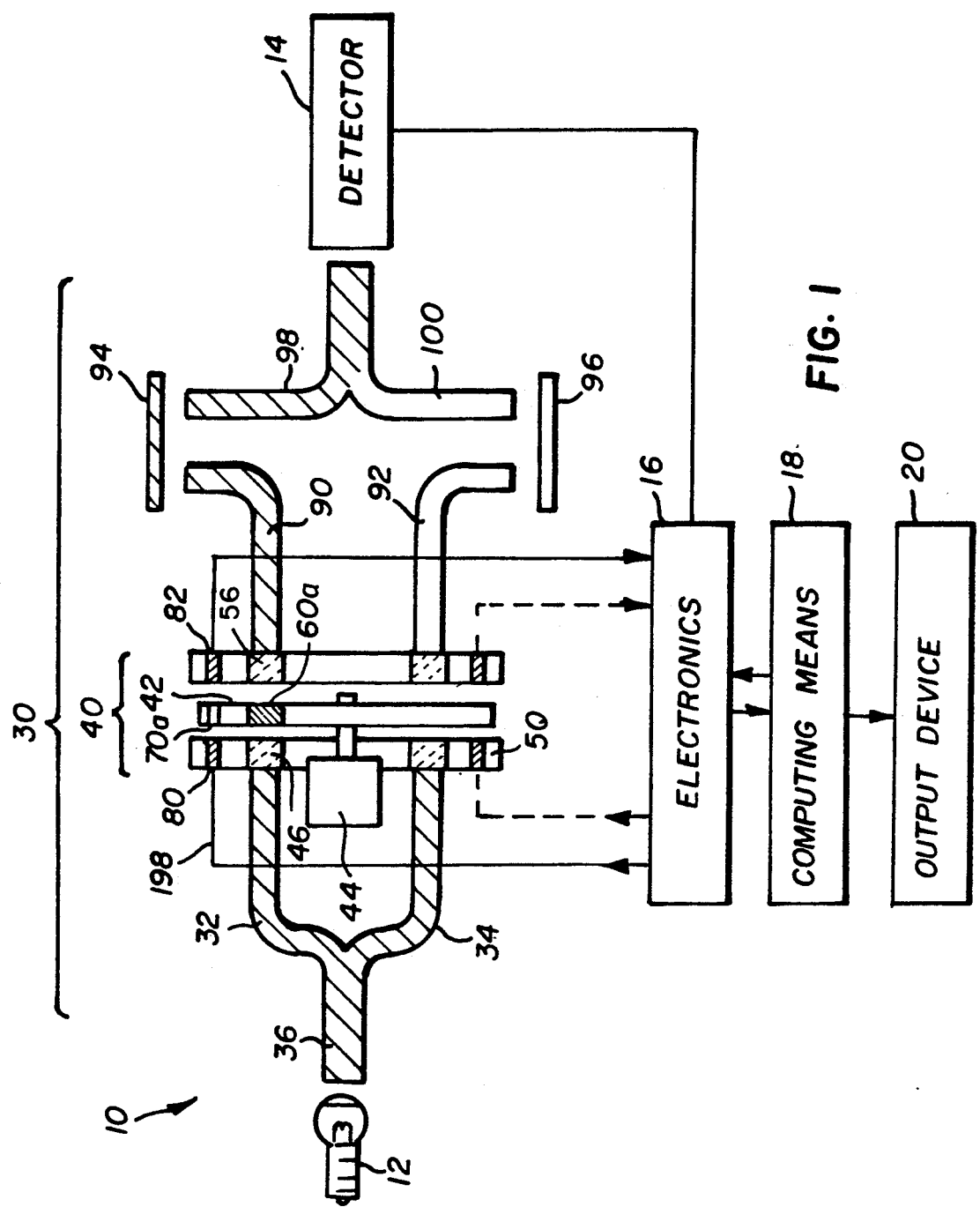
FIG. 1 is a schematic view of the overall construction of the spectrophotometer of the invention, shown at the stage when only the sample is being illuminated.

FIG. 1 illustrates the overall general configuration of spectrophotometer 10. It includes a light source 12 of any construction, a detector 14, associated electronics 16, computing means 18 and an output device 20. Optic means 30 are also provided for splitting the light from source 12 into two beams—beam 32 for the sample and beam 34 for the reference. Most preferably, optic means 30 comprise any optical fiber conduit 36 that is bifurcated into the two parts that confine beam 32 and 34.

Optic means 30 further include a control sector 40 which controls which of beams 32 and 34 passes onto its target, described hereinafter, and additional optical fibers 90 and 92 that deliver either the sample beam to sample 94, or the reference beam to reference 96, respectively. Pick-up fiber optics 98 and 100 relay reflected light from sample 94 and reference 96 to detector 14.

The preferred arrangement, as shown, is one in which the control sector 40 interrupts beams 32 and 34 before they illuminate either the sample 94 or reference 96. Alternatively (not shown), the invention can be used in an arrangement in which control sector 40 interrupts only the beam 98 and 100 carrying reflected light from the sample and reference, to the detector.

The components for light source 12, detector 14 and optical fiber conduits 36, 90, 92, 98 and 100 are all conventional and can be selected from a variety of known alternatives. Further description is unnecessary.

In accordance with one aspect of the invention, control sector 40 of optic means 30 comprises a chopper 42 rotated by motor 44 so that pass-through apertures alternate between the beams 32 and 34 delivered by conduit 36, as monitored by electronics 16. More specifically, FIG. 2, the fiber optic bundles confining beams 32 and 34 each terminate at ends 46 and 48, respectively, embedded in a first stationary plate 50. A second stationary plate 52 is held opposite plate 50 by a housing 54, and plate 52 holds ends 56 and 58 which are the initation points of fiber optics 90 and 92. Ends 56 and 58 of fiber optics 90 and 92 are aligned with ends 46 and 48, respectively. Preferably, ends 46 and 48, or 56 and 58, are wave guide materials, such as quartz rods or GRIN lenses.

Figure 3A:
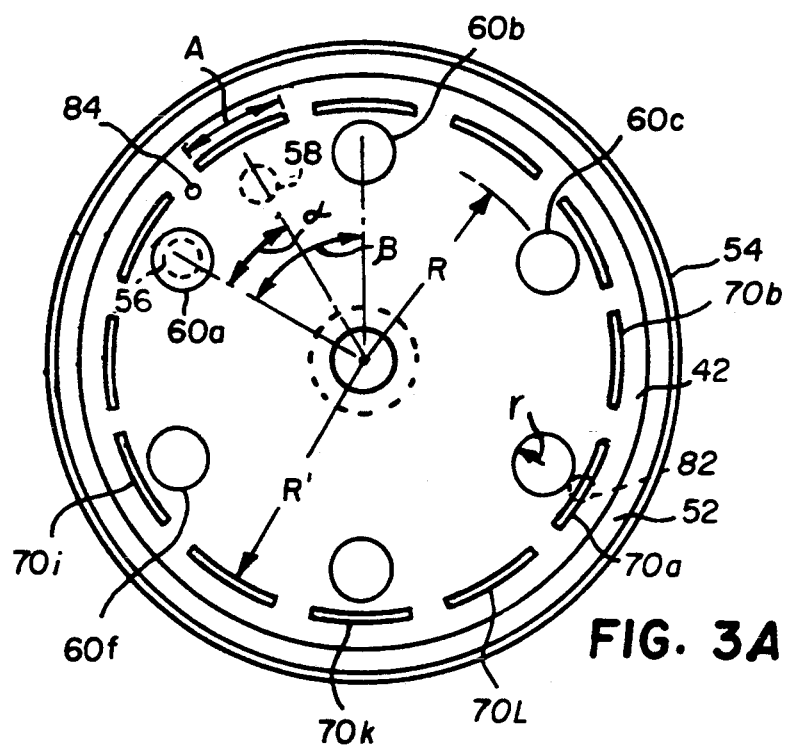
FIG. 3A and 3B is a section view taken generally along the line III—III of FIG. 2.
Figure 3B:
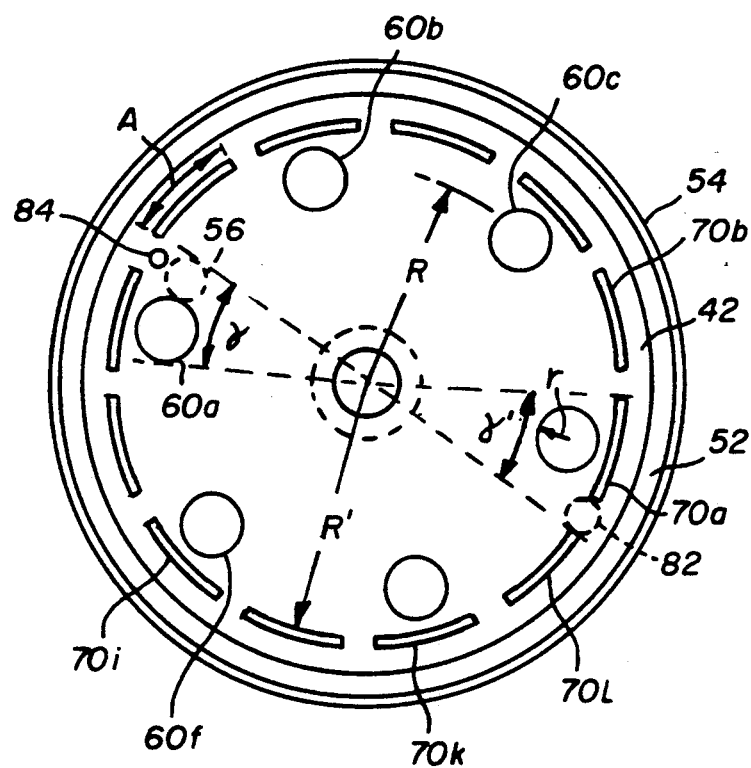

A critical aspect of the invention is chopper 42, as is more clearly shown in FIG. 3. Pass-through apertures 60a, 60b, 60c, 60d, 60e and 60f are provided in chopper 42, each containing a bandpass filter of a different, preselected band of wavelengths. For example, the filter in aperture 60a can pass the wavelengths 1296±5 nm, the one in aperture 60b the wavelengths 1360±5 nm, and so forth. Each aperture has a radius of dimension "r" Apertures 60a, 60b, 60c, 60d, 60e and 60f are disposed with their centers on a radius R, and preferably angularly disposed evenly about the 360° Most preferably, their angular disposition is at an angle $\beta$, which is larger than the angle $\alpha$ of the disposition of ends 56 and 58 of fiber optic bundles 90 and 92, and hence of the angular disposition of the illumination spots provided by beams 32 and 34. As shown, the values of $\alpha$ and $\beta$ are 30° and 60°, respectively.

At a different radius $R^1$ are located trigger means for sensing when a pass-through filter is aligned with one of the light beams. Such trigger means comprise, in cooperative combination, a suitable number of energy emitters and detectors, and energy relays on the chopper that periodically allow the energy of the emitter to reach the detector and not reach the detector. Most preferably, the energy relay is a slot to transmit light from a light emitter to a light detector, e.g., a photodetector, but alternatively, a reflector can be used to such energy.

In order to avoid the use of a separate moving part, e.g., a shutter, to alter which of the two beams is being detected, a particular relationship is needed between the number of pass-through apertures, the number of beams, the number of trigger energy emitter/diode combinations, and the number of relay means on the chopper for said trigger energy emitter/detectors. More specifically, if N=number of pass-through apertures (containing the filters), n=number of beams to be transmitted through the pass-through apertures, q=number of energy emitter/detector combinations, and Z=number of energy relay means on the chopper, the following equation holds:

(2) $n \times N = q \times Z$

Thus, for n=2 and N=6, $q \times Z = 12$. The maximum number of N of the pass through apertures is defined by the following formula:

$N < (L - d_2)/(d_1 + d_2 + 4r)$ wherein L=the total length of the chopper, r=the radius of the pass-through apertures, and $d_1$ and $d_2$=the diameter of the light beams for the reference and sample, respectively, so that the pass-through apertures are spaced apart a distance sufficient to ensure that, between each transmittal of one of said beams through the chopper, there is a time when no light beam is transmitted. One possibility in such a case is for q=1 and Z=12. That is, the energy relay means can comprise 12 slits, and one set of light emitter and detector. The 12 slits can be slits 70a, 70b, 70c, 70d, 70e, 70f, 70g, 70h, 70i, 70j, 70k and 70l (present in twice the number of the pass-through apertures 60a, 60b, 60c, 60d, 60e and 60f). (If yet a third beam, e.g. for a second sample, were passed through chopper 42, there would be, for q=1, three times the number of slits as there are apertures 60, and the value of alpha is preferably ⅓ that of beta). These slits have an arc A of open area that is at least equal to the dimension 2r of apertures 60a, 60b, 60c, 60d, 60e and 60f. Trigger slits 70a, 70b, 70c, 70d, 70e, 70f, 70g, 70h, 70i, 70j, 70k and 70l and radius $R^1$ are disposed so that the slits rotate between signalling means 80 and detector 82 on plates 50 and 52 respectively, FIG. 2. The angular disposition of signalling means 82, FIG. 3A, is such that the signal from means 80, 82 transmits through slit 70a when an aperture, e.g. 60a, is aligned with end 56 of the bundle 90 and transmits through slit 70b to detector 82 only when an aperture, e.g. 60a, is aligned with end 58 of the fiber bundle 92. To obtain optimum performance, the beam sizes and aperture widths should be such as to provide relative angles $\gamma$ and $\gamma'$, FIG. 3B, such that $\gamma' \geq \gamma$. As is apparent from FIG. 3B, $\gamma$ is that angle defined by $$\frac{A + dt}{R^1},$$

where dt is the smaller of the beam emanating from 80 and detected by 82, and $\gamma$ is that angle defined by $(2r + d)/R$, where d equals whichever beam diameter of 46, 56, 48 or 58 that is the largest diameter. The spectrophotometer will still function if $\gamma' < \gamma$, but the performance will be degraded.

Signalling means 80 and detector 82 are most preferably a light source and a photodetector, respectively, of conventional construction. However, other signal transmission means besides light can be used.

It will be readily appreciated that signalling means 80 and its detector 82 is effective to identify that an aperture 60 is in position, regardless of whether it is beam 32 or 34 that is being transmitted, by appropriately positioning the slit that is to signal that bundle 92 is aligned. If angle beta is not a whole integer multiple of angle alpha, then, e.g., slit 70l cannot be positioned halfway between slit 70a and slit 70k.

As will be seen from equation (2) above, q can also be=2, so that Z can be 6 (for $n \times N = 12$). Still further, q can equal 3 and Z equal 4, and in each case the relay means (e.g., slits) and positioning of the light emitters/detectors are preferably symmetric about the chopper.

Additionally, an aperture 84 is provided anywhere in chopper 42, for example at a radius that causes it to be positioned in between slits 70a, 70b, 70c, 70d, 70e, 70f, 70g, 70h, 70i, 70j, 70k and 70l, and apertures 60a, 60b, 60c, 60d, 60e and 60f. This cooperates with a separate pair of light source and detector 101, (FIG. 4) used to signal that chopper 42 is in the "home" position.

Slits 70a, 70b, 70c, 70d, 70e, 70f, 70g, 70h, 70i, 70j, 70k and 70l function as triggering and integration slits. That is, when the first portion of a slit 70 is in position between signalling means 80 and detector 82 to transmit the signal, the instrument turns "on" electronics 16, FIG. 1, as described more hereinafter, to collect and integrate the amount of light received from either sample 94 or reference 96. When the slit no longer is between means 80 and detector 82 so that the pulse ceases, the integration is terminated. Other shaped apertures besides slits will also function, provided they serve as "on" and "off" triggers of the integration, as described. The integration alternates between the sample and the reference, repeatedly.

Alternatively, (not shown), slits 70a, 70b, 70c, 70d, 70e, 70f, 70g, 70h, 70i, 70j, 70k and 70l can be replaced with reflecting surfaces of a similar shape, which will reflect the light beam from means 80 back to a detector 82' located adjacent to signalling means 80. The remainder of chopper 42 is non-reflecting. It is also contemplated that one can combine the function of slits 70 and aperture 84 by replacing the slits with reflecting surfaces, one of which is darker or lighter than the others and appropriately clamping the output of the detector 82'.

In addition, however, it is preferred that the integrators be "zeroed" at a dark reading. To do so, it is preferred that an opaque portion of chopper 42 pass over both beams 32 and 34 in between each transmittance of one beam or the other through the chopper. (The clamping of the "zero" value to this dark reading is conventional). To do this, a large number of orientations is possible for the pass-through apertures and/or the trigger and integration apertures. However, for a given size radius R of the center of each pass-through aperture having a given radius r and for a given size of radius of the fiber optic bundle, there is a maximum number of such pass-through apertures which, when evenly distributed angularly at that radius R of centers, one cannot exceed without destroying the "dark time" which is needed (the time when neither the reference beam nor the sample beam transmits through the chopper). That relationship can be expressed as follows:

Let sf equal the distance between apertures 60 and sb the distance between beam ends 46 and 48 as measured along the arc between the centers of the filters and beams respectively. Since the radius of curvature of that arc is R, FIG. 3A, the angles between the apertures and beams, af and ab, will be sf/R and sb/R respectively. Assume that all the apertures 60 have the same diameter, df, and that the beam ends 46 and 48 have the same diameter, db. The optimum placement of the filters in apertures 60, chopper 42, will then be at af=360/n degrees, where n is the number of apertures. The optimum placement of the beams will be at ab=af/2. Other placements are possible, however, within the definition of a preferred embodiment. If one defines a "tolerance angle", at=(df+db)/R, then ab must obey, af-at >ab->at.

If ab is too large, both beams 32 and 34 will simultaneously illuminate separate apertures, e.g., 60a and 60b. If ab is too small, both beams will simultaneously illuminate the same aperture, e.g., 60a.

Additional placements of the beams are possible, but not as a preferred embodiment. These placements will be designated ab', and occur at ab'=ab+m*af where ab must satisfy the condition stated above, and m is an integer. These placements will result in the illumination of two or more apertures 60 by the sample beam 32 before illumination by the reference beam 34. The sequence would then be: W1S, W2S...W1R, W2R... while the preferred sequence would be W1S, W1R, W2S, W2R; where W1 designates wavelength 1, W2 designates wavelength 2, etc. while S designates sample and R designates reference.

The preferred spectrophotometer as shown has the following characteristics: N=6; R=5.65 cm; df=1.27 cm; db=0.6 cm.

It follows that, af=360/N=60 degrees ≧; at=(360/2*pi) (1.27+0.6)/5.65=20 degrees; 40≧ab≧20 degrees.

If the beams do not have the same diameter, then db=rb1+rb2, where rb1 and rb2 are the radii of the two beams. If the filters do not have the same diameter, then a more complicated relationship follows, which depends upon the number of filters and the distribution of their relative sizes, but generally df=rf$_1$+rf$_2$ where rf$_1$ and rf$_2$ are the radii of the largest two adjacent apertures.

The electronics components 16, FIG. 1, is more particularly illustrated in FIG. 4. Unless otherwise specified, all electrical components and circuits herein are conventional and are designed for optimum signal-to--noise ratios.

Thus, component 16 comprises the "home" photodiode 101, the integration detector or photodiode 102, a cycle counter 103 to count the total number of cycles between resets, and an amplifier 104 that receives a signal from detector 14, FIG. 1. The "dark clamp" circuit 106, FIG. 4, receives a signal from both integration photodiode 102 and amplifier 104, and feeds to a conventional multiplexer 108 that multiplexes the signal between nN integrators 110 for each of the N apertures 60 (here, n=2 and N=6), wherein N integrators are for the sample and the other N integrators are for the reference. Each integrator 110 then preferably feeds to an integrator buffer 112. From there the signal from each of the N integrator buffers 112 for the sample, assigned to a given wavelength filter, sends its signal to averaging means 18', which preferably a portion of computing means 18, FIG. 1, a conventional computer. Similarly each of N integrator buffers, FIG. 4, separately feeds a reference reading for a given wavelength filter, to averaging means 18', so that an average can be taken for each of sample readings at the assigned bandpass wavelengths, and for each of the reference readings at the assigned wavelengths. The final results are directed to output device 20.

Figure 2:
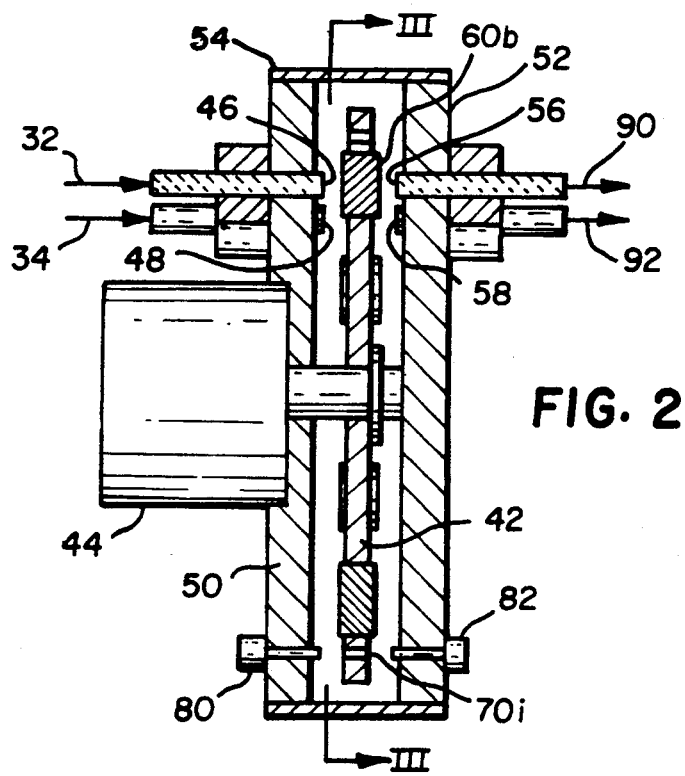
FIG. 2 is a section view of a portion of the optic means of FIG. 1, taken generally through the axis of rotation of the chopper of the spectrophotometer.

Alternatively, the averaging step and the use of means 18' can be omitted, so that an instantaneous reading of each integrator assigned to specific bandpass wavelengths, is sent to output 20 after a single revolution of chopper 42, FIG. 2.

Figure 5:
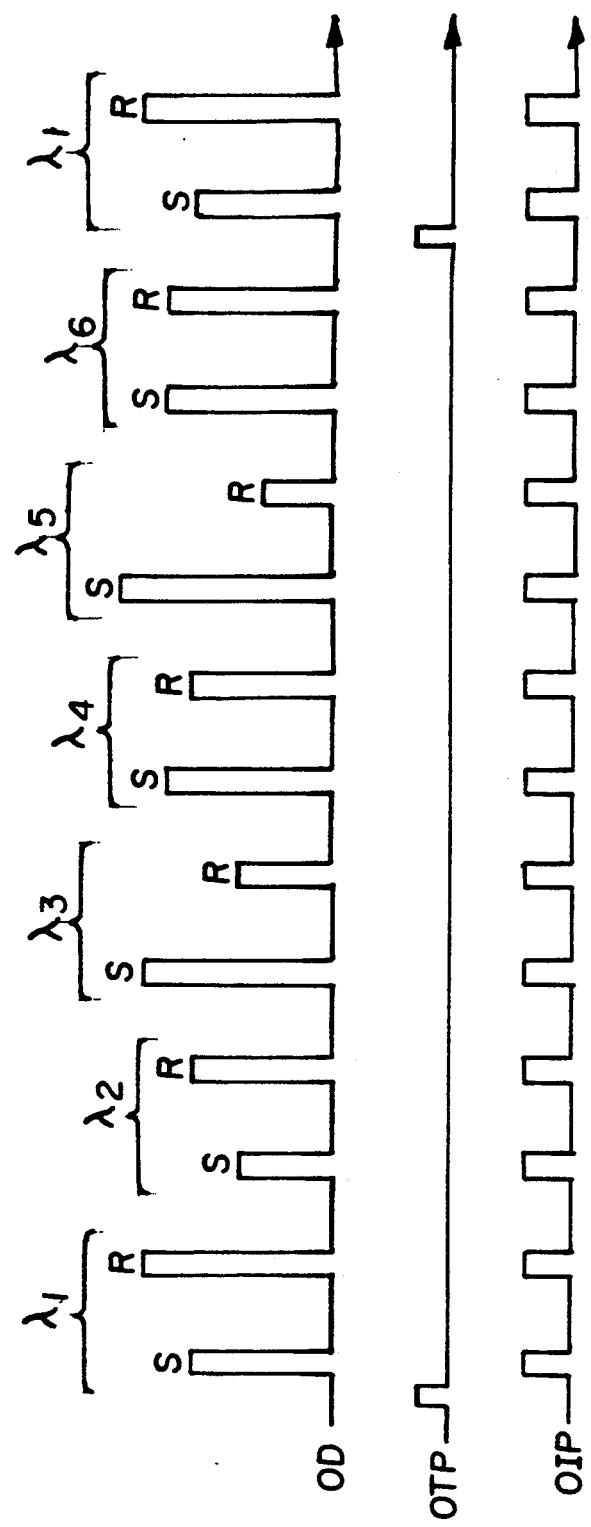
FIG. 5 is a schematic illustration of the outputs of the detector (OD), the home sensor (OTP) and the trigger or integration photodiodes (OIP)

The signal generated by the electronics components set forth in FIG. 4 is shown in FIG. 5. The width of the peaks of the OIP signal coming from detector 82 is preferably only slightly larger than the width of the peaks of the OD signal coming from detector 14, although the width of the OIP peaks could be greater since any dark reading before or after an aperture 60 transmits, should contribute no substantial signal. OIP signal widths that are less than the widths of the OD signal are not desired because performance is degraded. "S" represents a sample reading; whereas "R" is a reference reading. Each of the $\lambda_i$ values is, of course, a narrow range of values, rather than one single wavelength.

FIG. 6 further illustrates a preferred circuit for each of the 2 N integrators 110. They comprise an amplifier 114 that receives the signal A from multiplexer 108 through a resistor 116. Output B is used to charge capacitor 118 to a value that represents the actual light detected. The voltage created by that charge is then read through amplifier 120 and FET switch 122 and sent as the signal out that represents the reading for one complete set of cycles of chopper 42 at that bandpass wavelength.

Figure 7A:
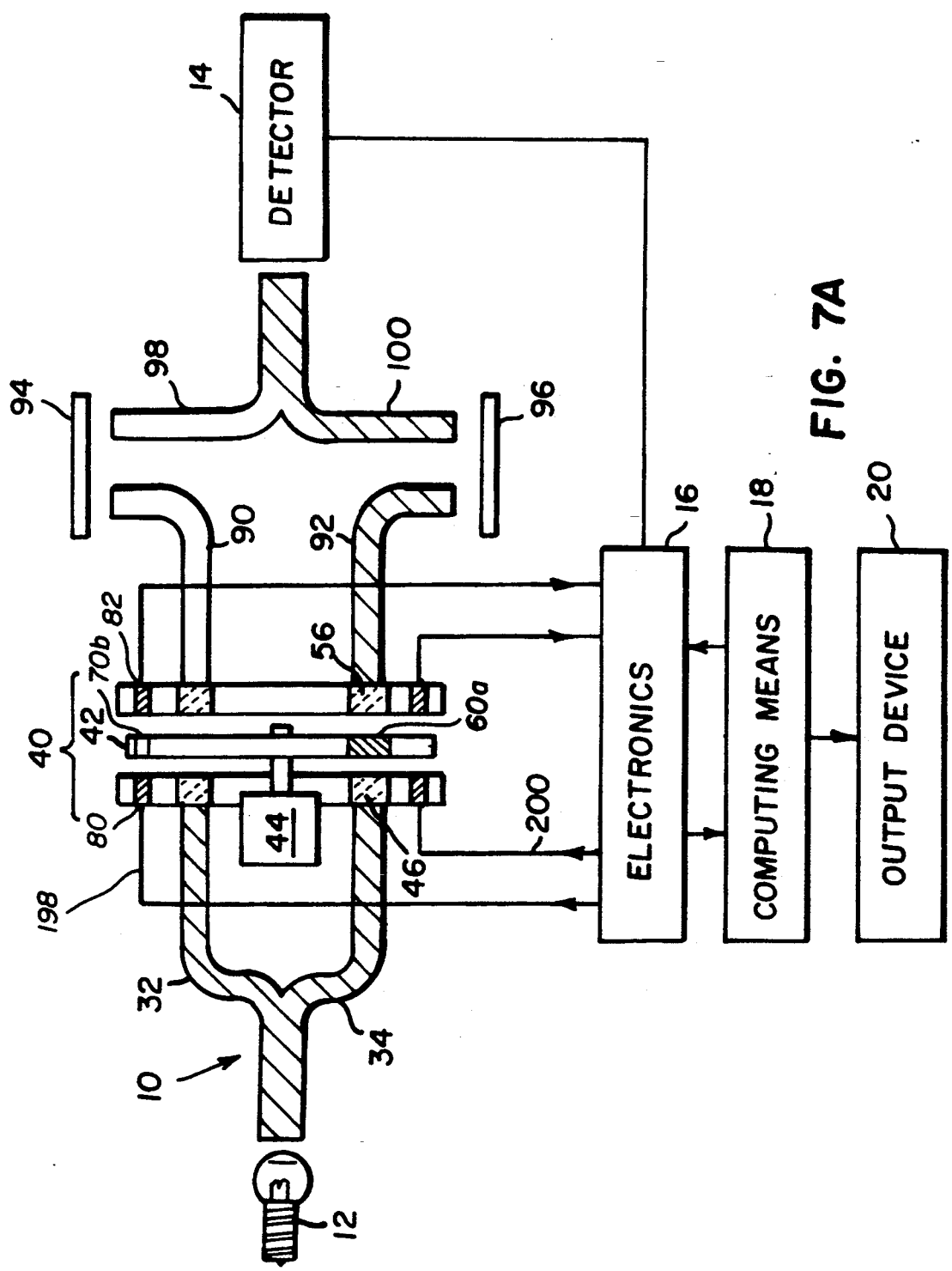
FIGS. 7A and 7B are views similar to that of FIG. 1, but illustrating the two other stages of operation of the spectrophotometer.
Figure 7B:
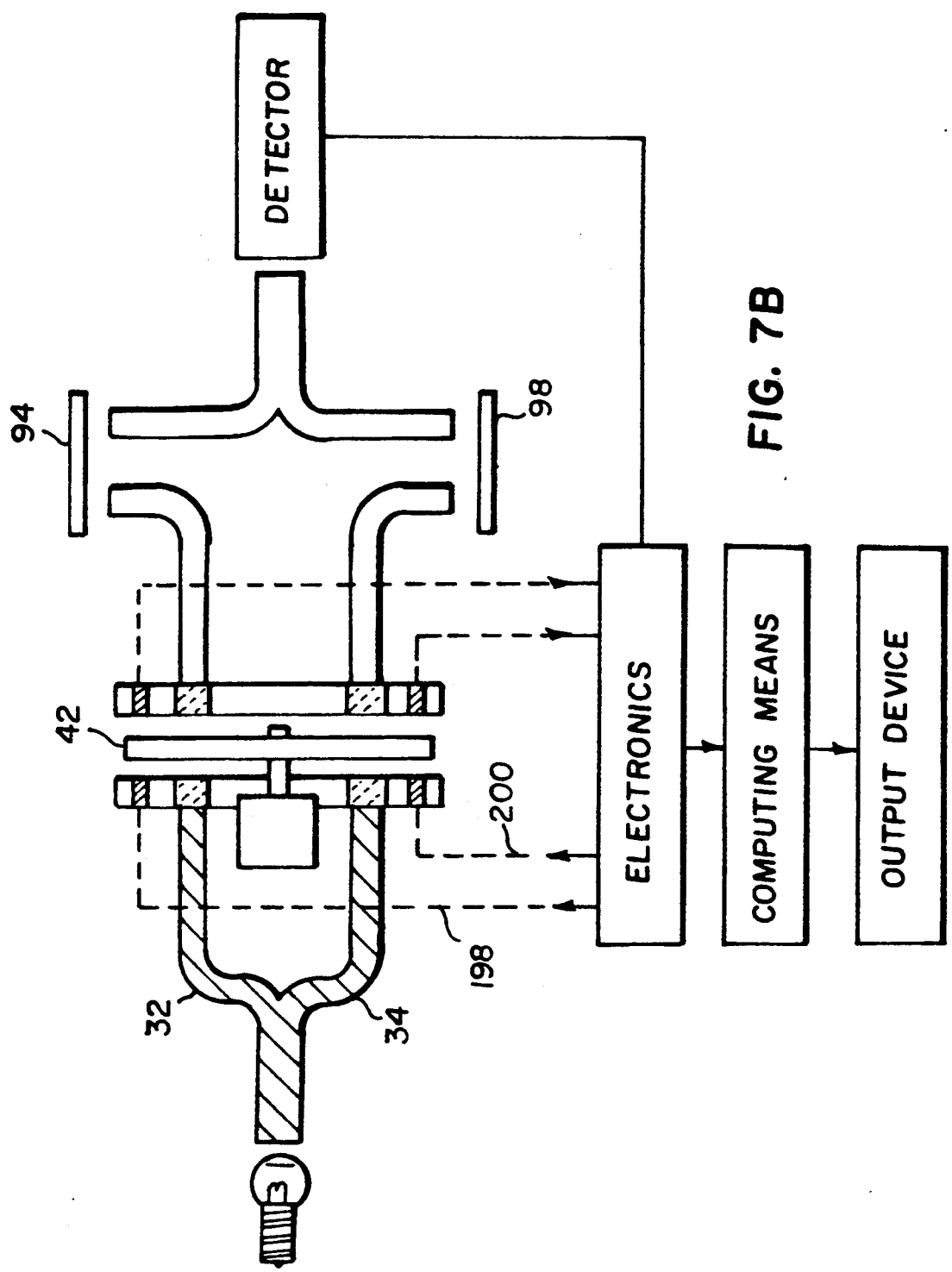

For completeness, FIGS. 7A and 7B are included to illustrate the spectrophotometer's two other states. In FIG. 7A, an aperture 60 is aligned only with beam 34 to transmit it to fiber bundle 92, which illuminates reference 96. (Only Sample 94 is illuminated in the configuration of FIG. 1. The integration of the light from that beam is controlled by slit 70a, as suggested by solid arrow 198). The alignment of a slit 70b between signalling means 80 and detector 82, arrow 198, allows the amount of light from beam 34 to be integrated. In FIG. 7B, no aperture 60 of chopper 42 is aligned with either beam or 34, and similarly, there is no transmission via arrow 198 that causes the integrators of component 16 to activate. It is at this part of the cycle that the dark clamping occurs to zero the current.

Transmission line 200 is used for scanning the home aperture 84.

It will be readily appreciated that, by a comparison at each of N different groups of wavelengths, of the sample signal against the reference signal, a determination can be made, using conventional mathematics, of the presence (and amount) of certain chemicals that are present at the sample. Most importantly, this is accomplished with a single light source and detector, to minimize drift, and optics to include a reference reading, and only one moving part (chopper 42) to minimize breakdowns. By having the reference be read very close in time to the sample read, e.g. within a few microseconds for chopper 42 being rotated at 1500 RPM, the potential for drift is further minimized.

It will also be appreciated that the aforedescribed spectrophotometer can be constructed without any mirrors or lenses being present. This provides the advantage of ruggedness and absence of alignment problems that otherwise occur. However, the other advantages of the invention of reliability and lack of drift can still be achieved even if a lens or mirror is included.

EXAMPLE

The following are exemplary, non-limiting illustrations of component parts useful in the construction of the spectrophotometer:

Light Source 12:
  Tungsten-halogen Lamp
  Welch Allyn Corp., Lamp Division
  Part #998079-14 12V, 18 Watt lamp with flame formed lens Fibers 90 & 92 and Randomized Bifurcated Fiber bundles 32, 34, 36, 98 and 100:
  Low OH silica fibers purchased from:
  Polymicro Technologies, Inc., Phoenix, Ariz.
  Part #FLP 200/220/240

Control Sector 40:
  Consists of the following components:
  Plate 50 and Plate 52 Constructed of 0.95 cm anodized aluminum
  Chopper 42 15.24 cm diameter, 0.32 cm thick anodized aluminum
  Filters in apertures 60:
    Model #100FC40 10 nm FWHM bandpass CWL tolerance of 2 nm 70% min. Transmission Blocking complete within 0.01% T. Wavelengths used are application dependent. When using 6 optical filters the following wavelengths (CWL) were used:
    1296 nm, 1360 run, 1472 run, 1536 run, 1678 run, 1722 nm Motor 44:
  Brushless DC Servo Purchased from Harowe Servo Control Co. Part #Motor-B1510H1339

Detector 14:
  Germanium Photodiode 2 mm Active area, BNC connector mounted Purchased from: EG&G/Judson Part #J16-LD-R02M It is not necessary that the chopper of this invention be rotated or that the path of the pass-through apertures be a circular path. As is shown in FIGS. 8A–8E, a linear chopper that is reciprocated works as well. Parts similar to those previously described bear the same reference numeral, to which the distinguishing suffix (quote marks) is appended.

Thus, the control sector 40" of the optics features a generally rectangular chopper 42" in which pass-through apertures 60a", 60b" and 60c" are provided, each with an appropriate filter. The chopper is caused to reciprocate, for example by a conventional stepper motor 300, FIG. 9, which rotates a lead screw 310, that in turn causes a carrier plate 320 to reciprocate, chopper 42" being attached to plate 320. This causes the chopper to reciprocate in front of both the sample beam 32" and the reference beam 34", here shown as the illumination spots that strike the chopper. (Alternatively, chopper 43" can be stationary and the beams caused to scan back and forth.)

The diameters of the two beams are $d_1$ and $d_2$ (shown here as being unequal), and of each filter, "2r". The filters are spaced a distance sf apart and the beams are spaced sb apart. The "+" designates the location of the integration detector 82" and the lines above the filters represent the integration slots 70a", 70b", 70c" 70d", 70e" and 70f" used in the energy relay means or the equivalent reflective surfaces.

The necessary conditions for the array to function derive from the same requirements that apply to the circular version. FIG. 8A shows that the beam must fit completely between the filters during the leading part of a dark cycle. FIG. 8B shows alignment of the first (sample) beam with the first filter. The integration photodetector 82" aligns with an integration slit, thus informing the electronics that a beam is aligned with a filter. FIG. 8C shows that the filter (or largest filter in the array, if the filters are not the same size) must fit completely between the beams during the trailing part of a dark cycle. FIG. 8D shows alignment of the second (reference) beam with the first filter. The photodetector 82" is once again aligned with a slot. FIG. 8E is analogous to FIG. 8A except that it corresponds to the leading edge of the dark cycle corresponding to illumination through the second filter.

It follows from FIGS. 8A–8E that the length of the chopper 42", "L", must be greater than $\{N(d_1+d_2+4r)+d_2\}$ in order to meet the required conditions. That is $N<(L-d_2)/(d_1+d_2+4_4)$. Furthermore, the placement of the beams and filters must correlate with their sizes according to the inequality:

$$s_f-(d_f+d_b) \geqq s_b(d_f+d_b).$$

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A spectrophotometer comprising a single light source, a single detector, signal generating means responsive to said detector for generating a signal representing the amount of light detected by said detector, optic means for separately illuminating both a reference and a sample with a light beam from said source that is transmitted to said detector, said optic means including:
   i) a rotatable chopper,
   ii) means for rotating said chopper to intercept the light beam, said optic means being constructed to alternately pass through said chopper a light beam for said reference and a light beam for said sample, said chopper further including a plurality of pass-through apertures, each with a bandpass filter constructed to pass through said chopper only light of preselected wavelengths, said optic means being further constructed and positioned to direct said reference light beam and said sample light beam at illumination spots on said chopper that are aligned with the circle of rotation of said pass-through apertures, and
   iii) a plurality of trigger means for sensing when said pass-through filters are aligned with one of said light beams, said trigger means being separately operatively connected to said signal-generating means and comprising at least one energy emitter and energy detector coupled with energy relay members on said chopper that either allow detection of said energy or prevent detection,
wherein said illumination spots on said chopper are disposed at an angle that is smaller than the degrees of the angular separation of said pass-through apertures,
said energy emitter/detector combinations and said relay men%bets of said trigger means are present in the following relationship:

$$n \times N = q \times Z$$

wherein n=the number of said light beams, N=the number of said pass-through apertures, q=the number of said emitter/detector combinations, and Z=the number of said relay members,
said means for generating a signal includes nN integrators, wherein n and N have the same meaning as before, and means for multiplexing said signal between said integrators wherein each said integrator receives the signal for an individual combination of one of said light beams and one of said filters and said integrators are triggered on and off by said relay members.

2. A spectrophotometer as defined in claim 1, wherein q=1 and n=2.

3. A spectrophotometer as defined in claim 2, wherein said energy relay members comprise slits.

4. A spectrophotometer as defined in claim 1, wherein said chopper is the only moving part required in said spectrophotometer.

5. A spectrophotometer as defined in claim 1 or 2, wherein said optic means is free of lenses and mirrors, and comprises a bifurcated fiber optic.

6. A spectrophotometer as defined in claim 1 or 2, wherein said signal generating means comprise a multiplexer and a number of integrators equal to twice the number of said pass-through apertures, and further including means for averaging the integrated signal generated by light passed through any one of said pass-through apertures over a given time period and delivered to said detector via either said reference beam or said sample beam.

7. A spectrophotometer as defined in claim 1 or 2, wherein the spacing, number and size of said pass-through apertures is adjusted to ensure that, between each transmittal of one of said beams through said chopper, there is a time when no light beam is transmitted.

8. A spectrophotometer as defined in claim 7, wherein the maximum number N of said pass-through apertures is defined by the following formula:

$$N < 2\Pi R / (d_1 + d_2 + 4r)$$

wherein R=the radius of the centers of said pass-through apertures, r=the radius of said pass-through apertures, and $d_1$ and $d_2$=the diameter of said light beams for the reference and sample, respectively.

9. A spectrophotometer comprising a single light source, a single detector, signal generating means responsive to said detector for generating a signal representing the amount of light detected by said detector, optic means for separately illuminating both a reference and a sample with a light beam from said source that is transmitted to said detector, said optic means including a rotatable chopper and means for rotating said chopper to intercept the light beam, said optic means being constructed to alternately pass through said chopper a light beam for said reference and a light beam for said sample, said chopper further including a) a plurality of pass-through apertures, each with a bandpass filter constructed to pass through said chopper only light of preselected wavelengths, said optic means being further constructed and positioned to direct said reference light beam and said sample light beam at illumination spots on said chopper that are aligned with the circle of rotation of said pass-through apertures, and b) a plurality of trigger means for sensing when said pass-through filters are aligned with one of said light beams, said trigger means being separately operatively connected to said signal-generating means,
the improvement wherein the maximum number N of said pass-through apertures is defined by the following formula:

$$N < 2\Pi R / (d_1 + d_2 + 4r)$$

wherein R=the radius of the centers of said pass-through apertures, r=the radius of said pass-through apertures, and $d_1$ and $d_2$=the diameter of said light beams for the reference and sample, respectively, so that said pass-through apertures are spaced apart a distance sufficient to ensure that, between each transmittal of one of said beams through said chopper, there is a time when no light beam is transmitted.

10. A spectrophotometer comprising a single light source, a single detector, signal generating means responsive to said detector for generating a signal representing the amount of light detected by said detector, optic means for separately illuminating both a reference and a sample with a light beam from said source that is transmitted to said detector, said optic means including
i) a movable chopper,
ii) means for moving said chopper relative to the light beam, said optic means being constructed to alternately pass through said chopper a light beam for said reference and a light beam for said sample, said chopper further including a plurality of pass-through apertures, each with a bandpass filter constructed to pass through said chopper only light of preselected wavelengths, said optic means being further constructed and positioned to direct said reference light beam and said sample light beam at illumination spots on said chopper that are aligned with the path of movement of said pass-through apertures,
iii) a plurality of trigger means for sensing when said pass-through filters are aligned with one of said light beams, said trigger means being separately operatively connected to said signal-generating means and comprising at least one energy emitter and energy detector coupled with energy relay members on said chopper that either allow detection of said energy or prevent detection,
wherein said illumination spots on said chopper are disposed to fall at a spacing that is smaller than the separation of said passthrough apertures,
said energy emitter/detector combinations and said relay members of said trigger means are present in the following relationship:

$$n \times N = q \times Z$$

wherein n=the number of said light beams, N=the number of said pass-through apertures, q=the number of said emitter/detector combinations, and Z=the number of said relay members, said means for generating a signal includes nN integrators, wherein n and N have the same meaning as before, and means for multiplexing said signal between said integrators wherein each integrator is assigned the signal for an individual combination of one of said light beams and one of said filters, and said relay members trigger said integrators on and off.

11. A spectrophotometer comprising a single light source, a single detector, signal generating means responsive to said detector for generating a signal representing the amount of light detected by said detector, optic means for separately illuminating both a reference and a sample with a light beam from said source that is transmitted to said detector, said optic means including a movable chopper and means for moving said chopper to intercept the light beam, said optic means being constructed to alternately pass through said chopper a light beam for said reference and a light beam for said sample, said chopper further including a) a plurality of pass-through apertures, each with a bandpass filter constructed to pass through said chopper only light of preselected wavelengths, said optic means being further constructed and positioned to direct said reference light beam and said sample light beam at illumination spots on said chopper that are aligned with the path of movement of said pass-through apertures, and b) a plurality of trigger means for sensing when said pass-detection through filters are aligned with one of said light beams, said trigger means being separately operatively connected to said signal-generating means, wherein the maximum nun%her of N of said pass through apertures is defined by the following formula:

$$N < (L - d_2)/(d_1 + d_2 + 4r)$$

wherein L=the total length of the chopper, r=the radius of said pass-through apertures, and $d_1$ and $d_2$=the diameter of said light beams for the reference and sample, respectively, so that said pass-through apertures are spaced apart a distance sufficient to ensure that, between each transmittal of one of said beams through said chopper, there is a time when no light beam is transmitted, said means for generating a signal includes nN integrators, wherein n and have the same meaning as before, and means for multiplexing said signal between said integrators wherein each integrator is assigned the signal for an individual combination of one of said light beams and one of said filters, and said relay members trigger said integrators on and off.

* * * * *

UNITED STATES PATENT AND TRADEMARK OFFICE
CERTIFICATE OF CORRECTION

PATENT NO. : 5,357,343
DATED : October 18, 1994
INVENTOR(S) : Alan J. Lowne, et. al.

It is certified that error appears in the above-indentified patent and that said Letters Patent is hereby corrected as shown below:

Column 11, line 8, change "men%bets" to --members--

Column 14, line 6, change "nun%her" to --number--.

Signed and Sealed this

Thirteenth Day of December, 1994

Attest:

BRUCE LEHMAN

Attesting Officer     Commissioner of Patents and Trademarks